United States Patent
Allinson et al.

(10) Patent No.: US 10,249,063 B2
(45) Date of Patent: Apr. 2, 2019

(54) METHOD AND APPARATUS FOR PROTON COMPUTERISED TOMOGRAPHY

(71) Applicant: University of Lincoln, Lincoln (GB)

(72) Inventors: Nigel Allinson, Lincoln (GB); Phil Evans, Guildford (GB); Gavin Poludniowski, Guildford (GB)

(73) Assignee: University of Lincoln, Lincoln (GB)

( * ) Notice: Subject to any disclaimer, the term of this patent is extended or adjusted under 35 U.S.C. 154(b) by 0 days.

(21) Appl. No.: 15/500,371

(22) PCT Filed: Jul. 30, 2015

(86) PCT No.: PCT/GB2015/052208
§ 371 (c)(1),
(2) Date: Jan. 30, 2017

(87) PCT Pub. No.: WO2016/016653
PCT Pub. Date: Feb. 4, 2016

(65) Prior Publication Data
US 2017/0221230 A1    Aug. 3, 2017

(30) Foreign Application Priority Data
Aug. 1, 2014 (GB) .................................. 1413729.3

(51) Int. Cl.
*G06T 11/00* (2006.01)
*A61B 6/03* (2006.01)
(Continued)

(52) U.S. Cl.
CPC ............ *G06T 11/003* (2013.01); *A61B 6/032* (2013.01); *A61B 6/4258* (2013.01);
(Continued)

(58) Field of Classification Search
None
See application file for complete search history.

(56) References Cited

U.S. PATENT DOCUMENTS

2011/0220794 A1   9/2011   Censor et al.
2012/0292517 A1   11/2012   Izaguirre
(Continued)

FOREIGN PATENT DOCUMENTS

DE   102 44 176 A1   4/2004
EP   0 421 869 A1   4/1991
(Continued)

OTHER PUBLICATIONS

Schulte et al. "Conceptual Design of a Proton Computed Tomography System for Applications in Proton Radiation Therapy", *IEEE Transactions on Nuclear Science* 51(3):866-872 (2004).
(Continued)

*Primary Examiner* — Vikkram Bali
(74) *Attorney, Agent, or Firm* — Myers Bigel, P.A.

(57) ABSTRACT

A method of reconstructing a 3-dimensional image in a proton transmission computerized tomography (CT) apparatus is disclosed. The method comprises the creation of a reconstruction matrix. The matrix is created by directing a plurality of particles to traverse the object; and for each particle, measuring the trajectory and energy of each particle before and after it has traversed the object; for each particle, calculating the water-equivalent path length within the object; and for each particle, calculating the positions at which it entered and exited the object; and adding the water-equivalent path length, entry and exit positions to the reconstruction matrix. This procedure is repeated from a plurality of angular positions surrounding an object to be imaged. Then, a spatially varying 2-dimensional filter function is applied to the reconstruction matrix. Subsequently, a correction factor is applied to the filtered reconstruction matrix to at least partially correct for the finite extent of the matrix.

20 Claims, 7 Drawing Sheets

(51) Int. Cl.
    A61N 1/16      (2006.01)
    G01N 23/046   (2018.01)
    A61B 6/00     (2006.01)
    G06T 7/00     (2017.01)
    A61N 5/10     (2006.01)

(52) U.S. Cl.
    CPC .............. *A61B 6/5205* (2013.01); *A61N 1/16* (2013.01); *G01N 23/046* (2013.01); *G06T 7/0012* (2013.01); *G06T 11/00* (2013.01); *A61N 2005/1087* (2013.01); *G01N 2223/107* (2013.01); *G01N 2223/419* (2013.01); *G06T 2207/10081* (2013.01)

(56) References Cited

U.S. PATENT DOCUMENTS

| | | |
|---|---|---|
| 2013/0015352 A1 | 1/2013 | Karonis et al. |
| 2017/0160211 A1* | 6/2017 | Schulte .................. G06T 11/006 |

FOREIGN PATENT DOCUMENTS

| | | |
|---|---|---|
| EP | 1 124 129 A2 | 8/2001 |
| EP | 2 279 776 A2 | 2/2011 |
| EP | 2 634 601 A2 | 9/2013 |
| JP | 63-40381 A | 2/1988 |
| WO | WO 2011/100628 A2 | 8/2011 |
| WO | WO 2013/116709 A1 | 8/2011 |

OTHER PUBLICATIONS

Combined Search and Examination Report, GB Application No. 1413729.3, dated Mar. 11, 2015 (5 pages).
Notification of Transmittal of the International Search Report and the Written Opinion of the International Searching Authority, or the Declaration, PCT/GB2015/052208, dated Oct. 16, 2015.
Afanaciev et al, "Investigation of the radiation hardness of GaAs sensors in an electron beam," IOP Publishing Ltd and Sissa Medialab, Nov. 2012, pp. 1-11.
Borchi et al., "The Compensation Condition in Hadron Calorimeters by the Filtering Effect," IEEE Transactions on Nuclear Science, vol. 37, No. 3, Jun. 1990, pp. 1186-1190.
Bruzzi et al., "Prototype Tracking Studies for Proton CT", IEEE Transactions on Nuclear Science, vol. 54, No. 1, Feb. 2007, pp. 140-145.
Bucciantonio et al., "Development of a fast proton range radiography system for quality assurance in hadrontherapy", Nuclear Instruments and Methods in Physics Research A, vol. 732, Dec. 2013, pp. 564-567.
Cirrone et al., "Monte Carlo Studies of a Proton Computed Tomography System," IEEE Transactions on Nuclear Science, vol. 54, No. 5, Oct. 2007, pp. 1487-1491.
Combined Search and Examination Report, GB Application No. 1410188.5, dated Dec. 18, 2014, 6 pages.
Combined Search and Examination Report, GB Application No. 1410206.5, dated Dec. 18, 2014, 8 pages.
Combined Search and Examination Report, GB Application No. 1410207.3, dated Dec. 12, 2014, 9 pages.
Cormack et al., "Quantitative Proton Tomography: Preliminary Experiments", Physics in Medicine & Biology, vol. 21, No. 4, Jul. 1976, pp. 560-569.
Cormack, "Representation of a Function by Its Line Integrals, with Some Radiological Applications", Journal of Applied Physics, vol. 34, No. 9, Sep. 1963, pp. 2722-2727.
Furetta et al., "Large-Area Sandwich Calorimeter for Hadronic Calorimetry," IEEE Transactions on Nuclear Science, vol. 35, No. 1, Feb. 1988, pp. 446-450.

Hurley et al., "Water-equivalent path length calibration of a prototype proton CT scanner," Med. Phys. 39 (5), May 2012, pp. 2438-2446.
Kim et al., "Study on Proton Energy Measurement by Using a Si(Li) Detector Stack," Journal of the Korean Physical Society, vol. 54, No. 5, May 2009, pp. 2050-2054.
Menichelli et al., "Characterization of a Silicon Strip Detector and a YAG:Ce Calorimeter for a Proton Computed Radiography Apparatus," IEEE Transactions on Nuclear Science, vol. 57, No. 1, Feb. 2010, pp. 8-16.
Notification of Transmittal of the International Search Report and the Written Opinion of the International Searching Authority, or the Declaration, PCT/GB2015/051690, dated Aug. 31, 2015, 13 Pages.
Notification of Transmittal of the International Search Report and the Written Opinion of the International Searching Authority, or the Declaration, PCT/GB2015/051691, dated Aug. 31, 2015, 12 Pages.
Notification of Transmittal of the International Search Report and the Written Opinion of the International Searching Authority, or the Declaration, PCT/GB2015/051692, dated Aug. 31, 2015, 13 Pages.
Pemler et al., "A detector system for proton radiography on the gantry of the Paul-Scherrer-Institute", Nuclear Instruments and Methods in Physics Research A, vol. 432, No. 2-3, Aug. 1999, pp. 483-495.
Pensotti et al, "Experimental results form a sandwich calorimeter using U-absorbers and 0.25m2 of Si active area," European Organization for Nuclear Research, Geneva, Jul. 11, 1987, 16 pages.
Poludniowski et al, "Proton-counting radiography for proton therapy: a proof of principle using CMOS APS technology," Phys. Med. Biol., vol. 59, 2014, pp. 2569-2581.
Rit et al., "Filtered backprojection proton CT reconstruction along with most likely paths", Medical Physics, vol. 40, No. 3, Mar. 2013, pp. 031103-1-031103-9.
Sadrozinski et al., "Detector Development for Proton Computed Tomography (pCT)", 2011 IEEE Nuclear Science Symposium Conference Record, Valencia, Spain, Oct. 23-29, 2011, pp. 4457-4461.
Sadrozinski et al., "Development of a head scanner for proton CT", Nuclear Instruments and Methods in Physics Research A, vol. 699, Dec. 2011, pp. 205-210.
Schulte et al, "Density resolution of proton computed tomography," Med. Phys., vol. 32, No. 4, Apr. 2005, pp. 1035-1045.
Schulte et al, "Design of a Proton Computed Tomography System for Applications in Proton Radiation Therapy," IEEE Nuclear Science Symposium. Conference, 2003, vol. 3, pp. 1579-1583.
Schulte et al., "A maximum likelihood proton path formalism for application in proton computed tomography", Medical Physics, vol. 35, No. 11, Nov. 2008, pp. 4849-4856.
Schulte et al., "Overview of the LLUMC/UCSC/CSUSB Phase 2 Proton CT Project," Trans Am Nucl Soc., 2012, vol. 106, 12 pages.
Simon, Frank, "Energy Reconstruction of Hadron Showers in the CALICE Calorimeters," IEEE Nuclear Science Symposium Conference Record, 2009, pp. 2292-2295.
Sipala et al., "A proton Computed Tomography system for medical applications", 14th International Workshop on Radiation Imaging Detectors, Figueira da Foz, Portugal, Jul. 1-5, 2012 (published Feb. 12, 2013), 7 pp.
Suzuki et al., "Comparison between an image reconstruction method of filtering backprojection and the filtered backprojection method", Applied Optics, vol. 27, No. 14, Jul. 15, 1988, pp. 2867-2870.
Wang et al., "On the use of a proton path probability map for proton computed tomography reconstruction", Medical Physics, vol. 37, No. 8, Aug. 2010, pp. 4138-4145.
Williams, "The most likely path of an energetic charged particle through a uniform medium", Physics in Medicine & Biology, vol. 49, No. 13, Jul. 2004, pp. 2899-2911.
Zeng et al., "Can the Backprojection Filtering Algorithm by as Accurate as the Filtered Backprojection Algorithm", 1994 IEEE Nuclear Science Symposium and Medical Imaging Conference, Norfolk, VA, Oct. 30-Nov. 5, 1994, pp. 1232-1236.

* cited by examiner

METHOD AND APPARATUS FOR PROTON COMPUTERISED TOMOGRAPHY

RELATED APPLICATIONS

This application is a 35 U.S.C. § 371 national stage application of PCT Application No. PCT/GB2015/052208, flied on Jul. 30, 2015, which claims priority from Great Britain Patent Application No. 1413729.3 filed on Aug. 1, 2014, the contents of which are incorporated herein by reference in their entireties. The above referenced PCT International Application was published in the English language as International Publication No. WO 2016/016653 A1 on Feb. 4, 2016.

This invention relates to a method and apparatus for 3-dimensional image reconstruction in computerised tomography. More specifically, it relates to computerised tomographic image reconstruction and typically in image reconstruction for applications in hadron (e.g., proton) and ion beam therapy.

The most-frequently-used hadron particles for treatment of cancer through external beam radiotherapy are protons, so the description that follows will refer exclusively to protons. However, it should be noted that other types of hadron and ion beam radiation can be used, such as beams of carbon or helium ions. Embodiments of this invention may make use of such other types of radiation. Treatment planning for proton therapy is typically performed using proton ray tracing, which involves predicting the path of a proton beam through a subject. This, in turn, allows a therapist to modulate the energy of a proton beam being used for therapy such that the Bragg peak of the beam, which is the region of the beam at which maximum energy deposition from the beam occurs, lies at the location of a treatment site, such as a tumour.

Water-equivalent path length (WEPL) data derived from x-ray computerised tomography (CT) images plays an important role in treatment planning for target volume delineation, and in dose and range calculations. In existing systems, the conversion of X-ray CT Hounsfield units to proton stopping power is a significant source of error in the derived WEPL data, which leads to systematic range errors of 3-5% for soft tissue, and even higher for bone and lung tissues. Use of proton transmission CT instead of X-ray CT can reduce range uncertainties to below 1%, so ensuring much improved treatment planning and delivery, and hence patient outcomes.

The purpose of computerised tomography (CT) is to determine the internal structures of an otherwise opaque object. In transmission tomography, a beam of penetrative photons or particles impinges on the object, and if the energy of the photons or particles is sufficient the probability that they will emerge from the far side of the object is high. Proton CT is a form of transmission tomography, in which a beam of protons passes from a source through the object being imaged from various angles. Each beam is detected on the side of the body away from the beam source, and its detected intensity, energy or some other property is compared to that property at the source.

The most usual form of CT is known as "Filtered Back-Projection" (FBP). In this form, a reconstruction matrix is created using back-projection from a number of sample images taken from a plurality of angular positions surrounding an object that is to be imaged. In order to remove artifacts and blurring from the reconstructed image, the reconstruction matrix is subject to a filtering operation using a high-pass or ramp filter to eliminate this blurring. The combination of filtering and back-projection provides this method with its customary name—Filtered Back-Projection (FBP).

There are numerous variations on the basic FBP approach. Since any practical input data will contain noise, and a ramp filter with accentuate this noise, some form of low-pass filtering is introduced to reduce the noise. Thus, there is a trade-off between the ramp filter characteristics and the filtering for noise suppression. The mean-squared optimal solution to this problem is to employ a Wiener filter.

An alternative to FBP is known in which the order of some operations is reversed—that is back-projection is performed before filtering—this can be termed as Back-Projection Filtered (BPF), an example being disclosed in S. Suzuki and S. Yamaguchi, *Comparison between an image reconstruction method of filtering back projection and the filtered backprojection method*, Applied Optics 27(14):2867:2870 (1988).

Both FBP and BPF are analytic techniques, in that they solve the reconstruction problem of going from the Radon transform of an object (that is the measurements) to the reconstructed object (that is the 2-dimensional image slice) only using each element of the data only once. This is in contrast to more computationally demanding iterative or statistical approaches that arrive at a solution by cycling through all of the measured data many times to converge on a solution by reference to some cost function.

The reordering of the filtering and back-projection operations between FBP and BPF approaches has profound consequences. Within the technical field, FBP has been preferred over BPF for several reasons in addition to the use of only 1-dimensional filtering mentioned earlier.

More analytic results have been derived for FBP convolution kernels, since 1-dimensional integrals are easier to perform than 2-dimensional integrals. The BPF approach has hitherto had issues with quantitative accuracy, as described in G. L. Zeng and G. T. Gullberg, *Can the backprojection filtering algorithm be as accurate as the filtered backprojection algorithm*? Nuclear Science Symposium and Medical Imaging Conference 1994, IEEE Conference Record Vol. 3: 1232-1236 (1995).

With modern computing power, the somewhat increased computational demands of using 2-dimensional Fourier transforms for filtering in BPF need not be an issue.

Unlike x-rays (photons), protons undergo multiple scattering as they pass through an object. This means that their trajectories are highly non-linear. Since it performs the filtering operation after back-projection, BPF is naturally more suited to non-linear projection paths than FBP.

In proton CT, the trajectory and residual energy after passing through an object needs to be recorded for individual protons and not ensembles, BPF naturally manages list-mode data (that is particles are considered singly and serially). The back-projection of each proton can be made onto a regular matrix in image space regardless of the curved trajectories.

The above factors make BPF very suited to proton CT.

The concept of proton CT is long-known [A. M. Cormack, "*Representation of a Function by Its Line Integrals, with Some Radiological Applications*," J. Appl. Phys. 34:2722 (1963)] but the optimal approach to reconstruction is still undecided [V. Sipala, M. Bruzzi, M. Bucciolini, M. Carpinelli, G. A. P. Cirrone, C. Civinini, G. Cuttone, D. Lo Presti, S. Pallotta, C. Pugliatti, N. Randazzo, F. Romano, M. Scaringella, C. Stancampiano, C. Talamonti, M. Tesi, E. Vanzif and M. Zanid, "*A proton Computed Tomography system for medical applications*," J. INST 8:C02021 (2013);

S. Rit, G. Dedes, N. Freud, D. Sarrut, J. M. Letang, "*Filtered backprojection proton CT reconstruction along most likely paths,*" Med Phys. 40(3):031103 (2013)]. In the most advanced embodiment of proton CT, data acquisition, measurements of the incoming and outgoing properties of each proton are made such that the most probable non-linear path of the proton through the object can be estimated. This enables improved spatial resolution in the final images. It is not clear how to best formulate optimal reconstruction in a FBP system. Firstly, there is a need to bin the protons somehow into regularly-spaced matrices. It is not clear how this should be done for curved paths because what would be an optimal rebinning for one voxel (spatial position) may not be for another. Researchers have tried applying strict cuts to the proton trajectories, discarding protons that are very curved in path [V. Sipala, M. Bruzzi, M. Bucciolini, M. Carpinelli, G. A. P. Cirrone, C. Civinini, G. Cuttone, D. Lo Presti, S. Pallotta, C. Pugliatti, N. Randazzo, F. Romano, M. Scaringella, C. Stancampiano, C. Talamonti, M. Tesi, E. Vanzif and M. Zanid, "*A proton Computed Tomography system for medical applications,*" JINST 8:C02021 (2013)]. Voxel-specific rebinning has been proposed but it is complex and a computationally expensive operation [S. Rit, G. Dedes, N. Freud, D. Sarrut, J. M. Letang, "*Filtered backprojection proton CT reconstruction along most likely paths,*" Med Phys. 40(3):031103 (2013).].

The BPF approach completely sidesteps this issue in an elegant manner. No rebinning prior to back-projection is necessary. The back-projection of each proton can be made onto a regular matrix in image space regardless of the curved trajectories.

The present inventors have realized that it should be possible to overcome the recognised disadvantages and difficulties involved with BPF, so the approach could be advantageously applied to proton CT An aim of this invention is to provide a computerised tomography method, system and apparatus that implements a new form BPF, so gaining its advantages, being implemented in a manner that makes efficient and effective use of computational resources.

From a first aspect, this invention provides a method of image reconstruction in computerised tomography comprising:
i. creating a reconstruction matrix by:
  from a plurality of scan angular positions surrounding an object to be imaged:
  i) directing a plurality of particles to traverse the object; and
  ii) for each particle, measuring the trajectory and energy of each particle before and after it has traversed the object;
  iii) for each particle, calculating an equivalent path length within the object; and
  iv) for each particle, calculating the positions at which it entered and exited the object; and
  v) adding the equivalent path length to the entry and exit positions of the reconstruction matrix or a subset of elements thereof;
ii. applying a 2-dimensional filter function to the reconstruction matrix; and
iii. applying a correction factor to the filtered reconstruction matrix to at least partially correct for the finite extent of the matrix.

In a typical embodiment of the invention, the particles are hadrons, and, in particular, protons.

The equivalent path length is typically an equivalent path length in a reference material; the most commonly used being the water-equivalent path length.

The trajectories of individual particles before traversal of the object are typically recorded by a multiplicity of position-sensitive detectors that are encountered by the particles before they encounter the object. Likewise, the trajectories of individual particles after traversal of the object are typically recorded by a multiplicity of position-sensitive detectors that are encountered by the particles after they have encountered the object.

For example, each measured particle trajectory is traced back to create an image reconstruction matrix, and there is deposited at each location within this matrix the corresponding values of the integral:

$$b(x, y) = \int_{-R}^{R} \int_{0}^{\pi} dt\, d\theta\, p(t, \theta) \delta(x \cos\theta + y \sin\theta - t) = \int_{0}^{\pi} d\theta\, p(t, \theta) \Big|_{x\cos\theta + y\sin\theta = t}.$$

In such embodiments, the creation of the reconstruction matrix is preferably completed prior to any filtration being applied to its contents.

In preferred embodiments of the invention, back-projected image matrix is given by:

$$b(i, j, k) = \frac{\pi}{L} \sum_{m=1}^{L} \frac{\sum_{n=1}^{K} \lambda_{n,m}(i, j, k) WEPL_{n,m}}{\sum_{n=1}^{K} \lambda_{n,m}(i, j, k)} b(i, j) = \frac{\pi}{L} \sum_{m=1}^{L} \frac{\sum_{n=1}^{K} \lambda_{n,m}(i, j) p_{n,m}}{\sum_{n=1}^{K} \lambda_{n,m}(i, j)}$$

where $\lambda_{n,m}(i, j, k)$ is the path length of the $n^{th}$ ray-projection through voxel $(i, j, k)$; L is the number of projection angles, and K is the number of recorded projections per angular position. This matrix may take different forms in other embodiments of the invention.

The image reconstruction matrix may be subject to a band-limited convolution kernel in which the sampling pitch of the matrix is imposed on this kernel in the frequency domain.

In preferred embodiments, the image reconstruction matrix is subject to a band-limited convolution kernel in which a sampling pitch of the matrix is imposed on this kernel in the frequency domain. An additional smoothing filter, such as a Shepp-Logan or a Gaussian filter, may be applied by sampling the appropriate function in the frequency domain and multiplying the kernel.

In preferred embodiments of the invention, in step b., the back-projected image matrix is convolved with a 2-dimensional filter function with may include the following kernel:

$$k(r) = \frac{1}{4\pi^2 r^3} \left[ \left(\frac{\pi r}{\tau}\right)^2 J_1\!\left(\frac{\pi r}{\tau}\right) - \Phi\!\left(\frac{\pi r}{\tau}\right) \right].$$

A further correction factor may be applied to the filtered reconstruction matrix to compensate for the finite extent of the reconstruction matrix and thereby improve the quantitative accuracy of the reconstructed images.

In preferred embodiments of the invention, in step c., the correction factor to the filtered reconstruction matrix is of the form:

$$\Delta = \left(\tau^2 \sum_{pixels \in \Omega_f} f(i,j)\right)\left(\tau^2 \sum_{pixels \notin \Omega_b} \frac{k(N/2-i, N/2-j)}{\tau\sqrt{i^2+j^2}}\right).$$

Other forms may be useful in alternative embodiments.

A further correction may be applied to further reduce residual errors in reconstructed stopping powers that arise from the trajectories of protons exiting the object to not being parallel to the collimation of the axis of the incident particle beam. Exiting protons may be projected back from the surface of the object to trajectories parallel to the primary beam axis.

From a second aspect, the invention provides computerised tomography apparatus comprising a source of particles, first detection means for detecting the position and energy of particles prior to their traversing an object, second detection means for detecting the position and energy of particles prior to their traversing an object, and analysing means configured to reconstruct an image of the object by analysis of output of the detection means using a method according to any preceding claim.

An embodiment of the invention will now be described in detail, by way of example, and with reference to the accompanying drawings, in which.

INTRODUCTION TO COMPUTERISED TOMOGRAPHY

Figure 1:
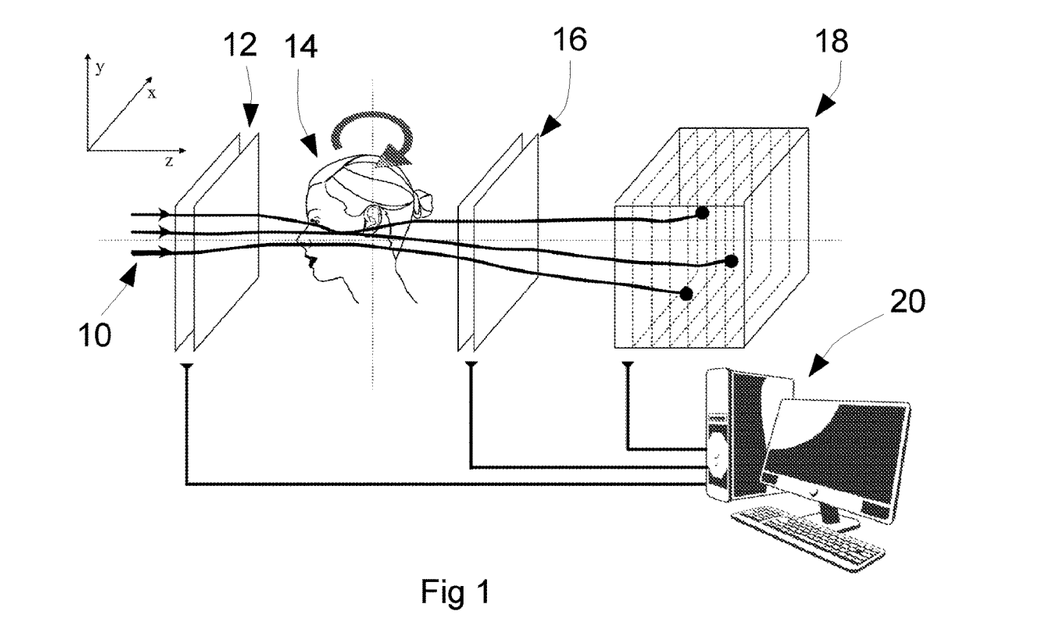
FIG. 1 shows an arrangement of a typical proton computerised tomography system.

FIG. 1 shows the arrangement of a typical proton CT system. A beam of protons 10 passes through one or more position-sensitive detectors 12 and from there to impinge upon an object or patient 14 to be imaged. If the energy of the protons is high enough, they will most likely pass through the object or patient 14 and emerge from the far side of the object or patient with some residual energy, $E_R$. The protons then pass through one or more position-sensitive detectors 16. The residual energy $E_R$ of the protons is then measured by an energy-sensitive detector 18. Data is collected from the detectors 12, 16, 18 and analysed by an associated computer system 20. The positions of individual protons as well as their residual energy, $E_R$, are recorded for a unique relative position of the patient relative to the system.

Either the patient or the instrument is rotated by a small scan angle, typically 1°-2°, about a central y-axis. The process is repeated over many scan angles.

Figure 2:
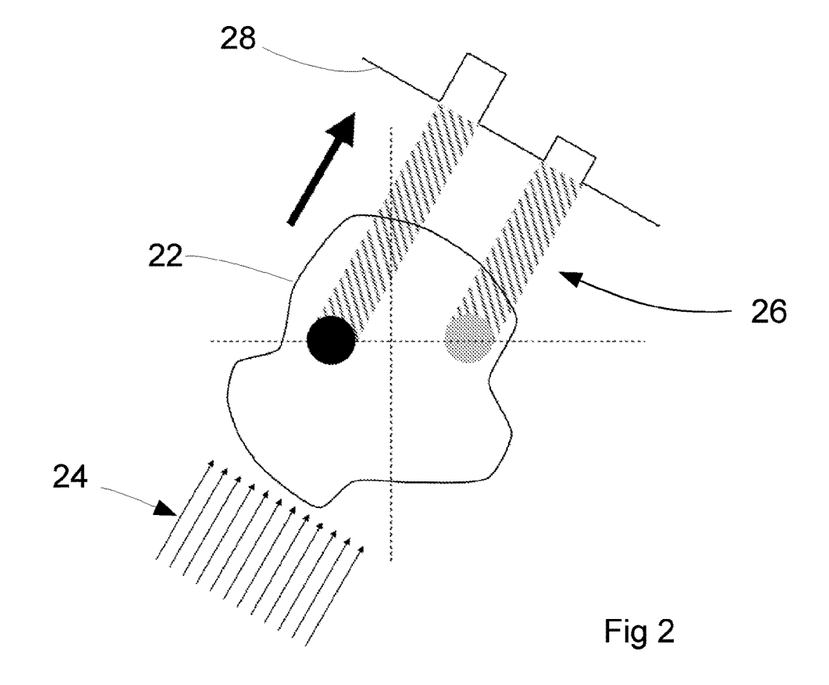
FIG. 2 is a diagrammatic illustration of the CT process.

If p is the transmittance of the object, then p is given by the line integral:

$$p = \int_L f(x,y) du,$$

where f(x, y) is some function of the object at the point (x, y) and L is the line along which the beam travels. CT scanners obtain p for various lines L, and use this information to compute an approximation to f(x, y) throughout the object. The principle is illustrated in FIG. 2, where an object 22 is illuminated by a beam 24 to produce a projection image 28.

In the two-dimensional case, the line L can be represented by the parameters r and θ, where θ measures the angle of the line from the vertical, and r measures the distance of the line from the origin of the (x, y) plane. The above formula is used to define a transform which maps a function f(x, y) to a function p(r, θ), where p(r, θ) is the line integral of f(x, y) over the line defined by r and θ. This transform is known as the Radon transform and denoted by $\mathfrak{R}$. The basic challenge of tomography is to reconstruct an image from its Radon transform. Fortunately, the Radon transform, when properly defined, has a well-defined inverse. In order to invert the transform, projection data spanning 180° is needed.

Figure 3:
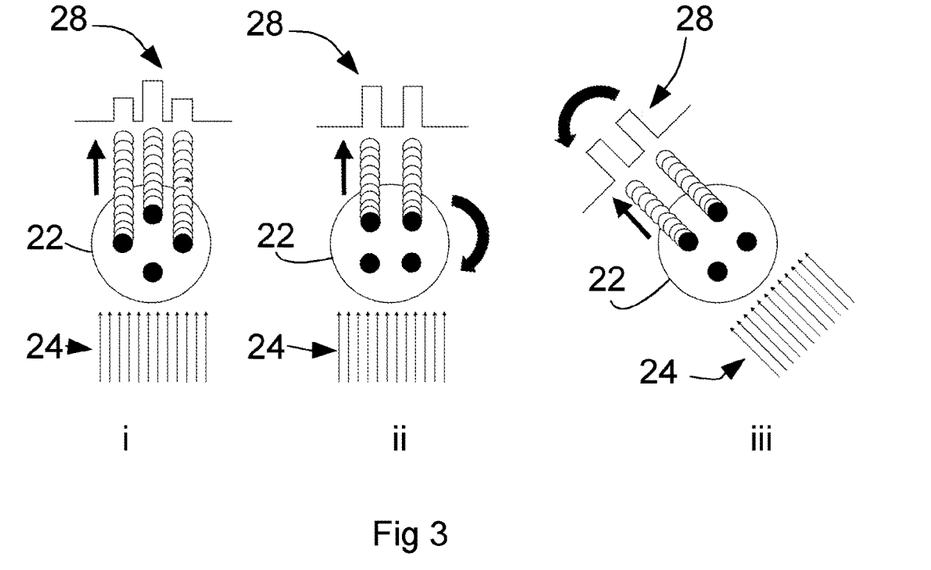
FIG. 3 shows alternative approaches to the production of multiple samples during the CT process.

The conventional approach to CT reconstruction is the Filtered Back Projection (FBP) method. The concept is explained in FIG. 3 (i), where the forward projected beam 24 and attenuated beam 26 of the object 22 is recorded as a projection image 28. FIG. 3 (ii) and (iii) show how other projection angles are obtained by either rotating the object with a fixed source and detector (FIG. 3 (ii)), or rotating the source and detector in tandem with a stationary object (FIG. 3 (iii)).

Figure 4:
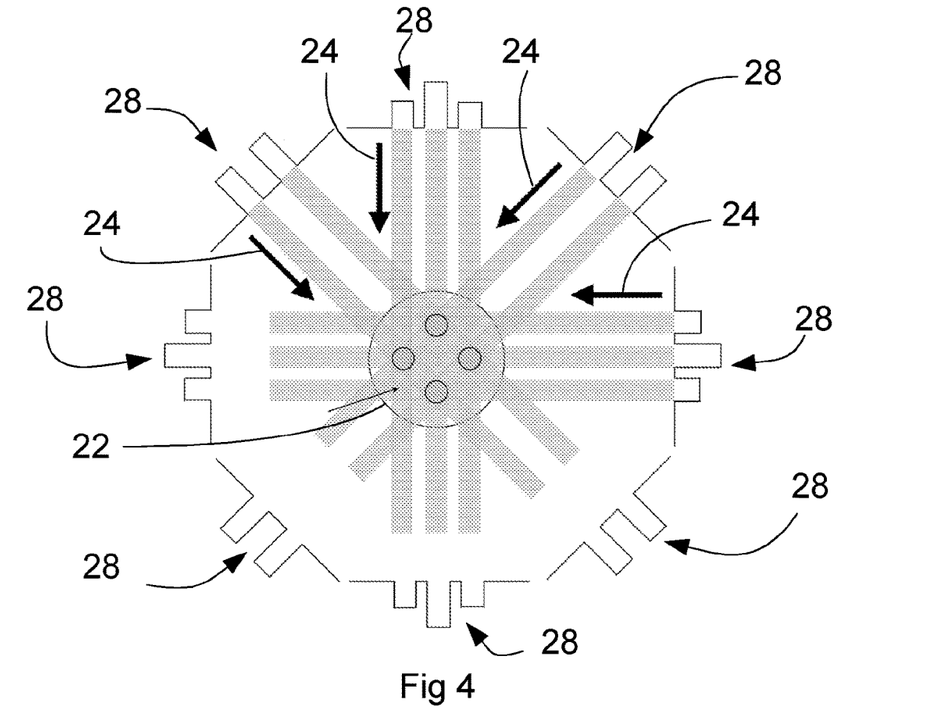
FIG. 4 is a diagrammatic illustration of the multiple samples during the CT process.

An arrangement that uses a finite number of (in this case, 8) sets of individual projection data from different scan angles then is as shown in FIG. 4. The individual projection images 28 are shown projected back through the image to obtain an estimate of the internal structures of the original object 22. The individual projections will interact constructively in regions that correspond to features in the original object 22.

A problem that arises from the arrangement of FIG. 4 is that blurring and star-like artifacts occur in other parts of the reconstructed image. A high-pass or ramp filter is used to eliminate this blurring. The combination of filtering and back-projection provides this method with its customary name: "Filtered Back-Projection" (FBP).

There are numerous variations on the basic FBP approach. Since any practical input data will contain noise, and a ramp filter will accentuate this noise, some form of low-pass filtering is introduced to reduce the noise. There is a trade-off between the ramp filter characteristics and the filtering for noise suppression. The mean-squared optimal solution to this problem is to employ a Wiener filter.

Hence, the essential steps in producing a CT image using FBP are:
1. Record with uniform sampling multiple individual projections through a 2-dimensional slice of an object to produce a 1-dimensional array.
2. Convolve this array of data with a 1-dimensional deblurring kernel (or the equivalent filtering in the spatial-frequency domain).
3. Back-project the convolved ray-projections through a 2-dimensional reconstruction matrix.
4. Repeat over many scan angles.

Figure 5:
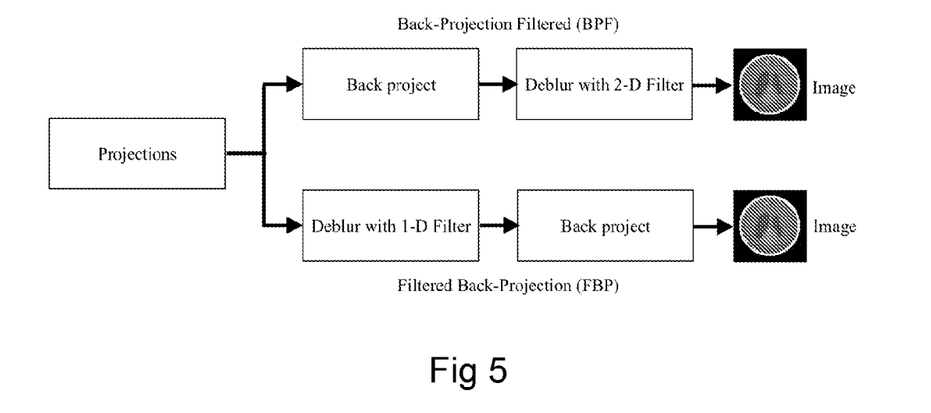
FIG. 5 is a comparison between FBP and BPF forms of CT.

An alternative to FBP is known in which the order of some operations is reversed—that is back-projection is performed before filtering—this can be termed as Back-Projection Filtered (BPF), an example being disclosed in S. Suzuki and S. Yamaguchi, *Comparison between an image reconstruction method of filtering backprojection and the filtered backprojection method*, Applied Optics 27(14):2867:2870 (1988). The two approaches are compared in FIG. 5. The BPF approach has not been used in practice because of the need for a computationally more complex 2-dimensional filter rather than a 1-dimensional one, and, without the techniques presented by the present invention, has been shown to be quantitatively less accurate.

The CT Proposal of this Embodiment

The embodiment of this invention implements a BPF using an analytic technique in to solve the reconstruction problem of going from the Radon transform of an object (that is the measurements) to the reconstructed object (that is the 2-dimensional image slice) only using each element of the data only once.

For parallel beam tomography the projections can be expressed as the Radon transform of the object that is to be reconstructed. The Radon transform is defined as:

$$p(t, \theta) = R(f) = \int_{-\infty}^{\infty}\int_{-\infty}^{\infty} f(x, y)\delta(x\cos\theta + y\sin\theta - t)dxdy$$

that is the line integral along a line at an angle $\theta$ from the y-axis and at a distance $|t|$ from the origin. By rotating the coordinate system:

$t = x\cos\theta + y\sin\theta$ $u = -x\sin\theta + y\cos\theta$

Then:

$$p(t, \theta) = \int_{-\infty}^{\infty} f(t\cos\theta - u\sin\theta, t\sin\theta + u\cos\theta)du.$$

This approach for reconstructing the image is to take the inverse Radon transform of the projections. This involves two steps: the image is back-projected and then filtered with a 2-dimensional filter.

The back-projection operator $\mathcal{B}$ is defined as:

$$\mathcal{B}(p) = \int_0^\pi p(x\cos\theta + y\sin\theta, \theta)d\theta$$

This operator represents the accumulation of the projections that pass through a point (x, y).

Hence, the essential steps in producing a CT image using BPF in this embodiment are:
1. Record (with not necessarily uniform sampling) individual projections through a 2-dimensional slice of an object to produce a 1-dimensional array. It is possible to relax this strict condition, namely that proton paths stay solely with a 2-dimensional plane.
2. Back-project the projections through a 2-dimensional reconstruction matrix.
3. Convolve (or filter) this 2-dimensional data matrix with a 2-dimensional deblurring kernel.
4. Repeat over many scan angles. The scan angles need not be uniformly distributed.

A formal treatment of the BPF approach embodying the invention will now be presented.

Figure 6:
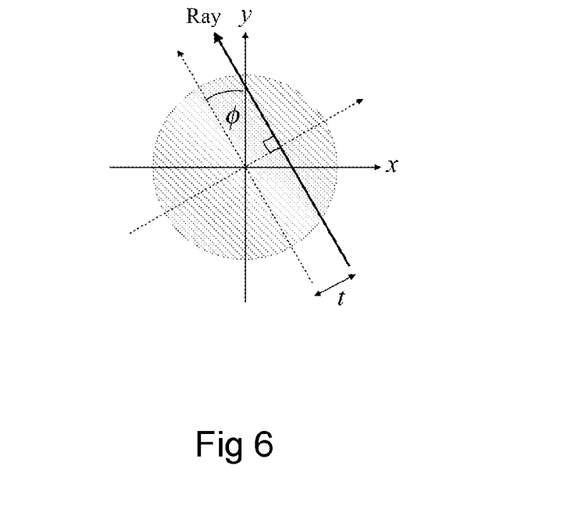
FIG. 6 is a diagram showing a proton beam passing through an object to be imaged.

Suppose a 2-dimensional slice of a body has some property described by the function, f(x, y), with a compact support, $\Omega_f = \{(x, y) \in \Re^2 : x^2 + y^2 < R^2\}$. In the case of proton CT, the appropriate property is the proton relative stopping power. A line integral through the object, at an angle $\theta$ and position t (see FIG. 6) can be written as:

$$p_\theta = \int_{-R}^{R}\int_{-R}^{R} dx\,dy\, f(x, y)\delta(x\cos\theta + y\sin\theta - t). \quad (1)$$

This line integral is a ray projection through a slice of an object being imaged, and is related to the path length in a reference material, typically the water-equivalent path length (WEPL). The presence in a body of a patient with many different tissues, each with its own density, represents a challenge to image reconstruction. The concept of WEPL gets around this problem as the water equivalent approximation is based on the fact that the stopping powers of different materials are very similar to one another. The transform from the space (x, y) to ($\theta$, t) is the Radon transform.

The back-projection operation is defined as:

$$b(x, y) = \int_{-R}^{R}\int_0^\pi dt\,d\theta\, p(t, \theta)\delta(x\cos\theta + y\sin\theta - t) = \quad (2)$$

$$\int_0^\pi d\theta\, p(t, \theta)\Big|_{x\cos\theta + y\sin\theta = t}$$

This is equivalent to tracing back along the ray-projection path and depositing, at each location through which it passes, the value of the line integral. The resulting back-projection function, b(x, y), resembles a blurred representation of the density function, f(x, y). In fact, they are related through:

$$b(x, y) = f(x, y) ** \frac{1}{r}, \quad (3)$$

where ** denotes a 2-dimensional convolution, and $r = \|(x, y)\|$. Note that the function b(x, y) has non-compact support: $\Omega = \{(x, y) \in \Re^2\}$. That is, it is non-zero everywhere.

This convolution relation can be expressed as a filtering operation in 2-dimensional Fourier space. Let the Fourier conjugate variables of (x, y) be (u, v) and $\rho = \|(u, v)\|$. Then, it is possible to write:

$$f(x, y) = FT^{-1}\left\{\frac{FT\{b\}}{FT\{r^{-1}\}}\right\} = IFT\{FT\{b\}\rho\}, \quad (4)$$

where FT and IFT indicates two 2-dimensional forward and inverse Fourier transforms respectively; and it is known that, in 2 dimensions:

$$FT\{r^{-1}\} = \rho^{-1}$$

In a practical implementation, a discrete formulation for the back-projected image, b, needs to be used. The 2-dimensional matrix for b can be calculated from a set of acquired measurements in several ways. One possible scheme will now be described.

Imagine that L projections are acquired over a set of different scan angles:

$$\left\{\phi_n = \pi\frac{l-1}{L}: l = 1, 2, \ldots, L\right\}.$$

At each scan angle, K ray-projections are sampled (not necessarily uniformly), with a set of locations: $\{t_k: k=1, 2, \ldots, K\}$. Now consider a discrete 2-dimensional back-projection matrix, b(i, j), with corresponding pixel centres $\{x_i = (2i-N-1)\tau/2: i=1, 2, \ldots, N\}$ and $\{y_j = (2j-N-1)\tau/2: j=1, 2, \ldots, N\}$ with τ being the matrix pitch. This matrix could be expressed in terms of the discrete Radon transform, $p_l(k)$ as follows:

$$b(i, j) = \frac{\pi}{L}\sum_{m=1}^{L}\frac{\sum_{n=1}^{K}\lambda_{n,m}(i, j)p_{n,m}}{\sum_{n=1}^{K}\lambda_{n,m}(i, j)}, \quad (5)$$

where $\lambda_k(i,j)$ is the path length of the $k^{th}$ ray-projection through the pixel (i, j). The 3-dimensional version with the 2-dimensional line integral replaced with the measured WEPL, is:

$$b(i, j, k) = \frac{\pi}{L}\sum_{m=1}^{L}\frac{\sum_{n=1}^{K}\lambda_{n,m}(i, j, k)WEPL_{n,m}}{\sum_{n=1}^{K}\lambda_{n,m}(i, j, k)}$$

This version relaxes the requirement for linear in-plane paths.

The filtering operation of this embodiment will now be described.

Two constraints must be imposed on the filtering operation: the sampling pitch and the finite size of the back-projection matrix. The first must be imposed on the filter in the frequency domain and then the second on the kernel in the spatial domain. The band-limit on spatial-frequencies is imposed by modifying the ramp filter representation of the kernel in frequency space:

$$K(\rho) = \rho \quad \text{if } \rho < \frac{1}{2\tau}$$
$$0 \quad \text{otherwise}$$

The relationship between the convolution kernel and filter involves a 2-dimensional Fourier transform (in contrast with the FBP procedure, which involves a 1-dimensional Fourier transform).

The 2D convolution kernel, k(r), is now derived as:

$$k(r) = IFT\{K(\rho)\} \quad (6)$$

$$= \int_0^{\frac{1}{2\tau}}\int_{-\pi}^{\pi}\rho d\rho d\phi \rho e^{j2\pi\rho r\cos(\theta-\phi)}$$

$$= 2\pi\int_0^{\frac{1}{2\tau}}d\rho\rho^2 J_0(2\pi r\rho)$$

$$= \frac{1}{4\pi^2 r^3}\left[\left(\frac{\pi r}{\tau}\right)^2 J_1\left(\frac{\pi r}{\tau}\right) - \Phi\left(\frac{\pi r}{\tau}\right)\right]$$

where $$\Phi(x) = \frac{\pi x}{2}[J_1(x)H_{0(x)} - J_0(x)H_{1(x)}]$$

and $J_n$ and $H_n$ are $n^{th}$ order Bessel and Struve functions, respectively. Note that this kernel remains finite at zero argument since:

$$k(r = 0) = \frac{\pi}{12\tau^3}$$

The finite size of the back-projection matrix and kernel must be considered in order to find the appropriate filter in the discrete Fourier space. The correct filter to use is a Discrete Fourier Transform (DFT) of the finite band-limited kernel derived above. This is:

$$K(I,J) = DFT\{k(i,j): i=-N, \ldots, N-1; j=-N, \ldots, N-1\}$$

where I and J are the discrete Fourier conjugate variables. The filtering operation is performed by multiplying the DFT of the back-projection matrix, b(i, j) by the DFT of k(i, j). That is:

$$f_{bpf} =$$
$$\left\{\begin{array}{c}DFT^{-1}\{b(i, j): i = 1, \ldots, N; j = 1, \ldots, N; \text{with zero points to } 2N\} * \\ DFT\{k(i, j: i = -N, \ldots, N-1; j = -N, \ldots, N-1)\}\end{array}\right\}$$

The process of finite matrix correction will now be described.

The mathematical formulation given above described the BPF process and how to implement it. However, this formulation may not allow the reconstruction of quantitatively accurate images of proton stopping power. Although f(x, y) is clearly zero outside of the desired reconstruction region, the function b(x, y) is non-zero everywhere. In practice, the support for back-projection must be bounded: $\Omega_b^T = \{(x, y) \in \Re^2: x^2 < R^2, y^2 < R^2\}$. The finite matrix size chosen for back-projection will result in truncation of the data.

Previously, the only attempt to deal with this problem has been to make the size of the back-projection matrix (N×N), much larger than the desired image matrix (M×M) with, say, N=4M. Such an approach is wasteful for computer memory and increases computation, as well as only asymptotically improving accuracy.

The effect of missing data, due to a finite back-projection matrix, closely resembles a zero-frequency offset in the reconstructed stopping-power f(i, j). The effect of distant data on the reconstruction region will only manifest itself at low-spatial frequencies. A constant-shift offset correction can be arrived at in several ways.

Consider the following: the distant values of the back-projection matrix (if far enough away from the central region) can be approximated as:

$$b(x, y) = f(x, y) ** \frac{1}{r} \simeq \int_{\in \Omega_f} dx' dy' \frac{f(x', y')}{\sqrt{(x-x')^2 + (y-y')^2}},$$

where r>>r'. The contribution to f(x, y) of the missing data is therefore approximately:

$$\Delta(x, y) = \int_{\notin \Omega_b} dx' dy' b_{r \gg r'}(x', y') k(x-x', y-y') \quad (9)$$

$$= \left( \int_{\in \Omega_f} dx' dy' f(x', y') \right) \left( \int_{\notin \Omega_b} dx' dy' \frac{k(x-x', y-y')}{r'} \right).$$

To the central pixel, (N/2, N/2), this becomes:

$$\Delta = \left( \tau^2 \sum_{pixels \in \Omega_f} f(i, j) \right) \left( \tau^2 \sum_{pixels \notin \Omega_b} \frac{k(N/2-i, N/2-j)}{\tau \sqrt{i^2+j^2}} \right). \quad (10)$$

The first summation is the sum of all the pixel values in the reconstructed image slice ($\in \Omega_f$). The second sum is a summation over all pixels outside the back-projection region ($\notin \Omega_b$).

This is in principle an infinite sum, but can be evaluated inexpensively to a desired accuracy. This correction, C, calculated for one pixel, is then applied to all pixels in the image as a constant offset, that is:

$$f_{Cor}(i,j) = f_{bpf}(i,j) + C. \quad (11)$$

It should be noted that the above formulation for reconstruction assumes linear in-plane ray-projections (in this case, proton paths). As such, each slice of the 3D volume should factorize into a separate 2D problems with distinct data. This is the essence of classical tomography. In reality, due to beam angular dispersion and straggling, protons will not typically remain in the same axial plane as they progress through an object. However, both the angular dispersion and straggling of protons are typically small enough to be considered a perturbation. Typical root-mean-square figures for beam divergence before and after a patient might be 5 mrad and 50 mrad respectively (Bruzzi M, et al. 2007, *Prototype Tracking Studies for Proton CT*, IEEE Trans. Nucl. Sci. 54, 140-145), although these values would depend on the beam nozzle design, proton energy and size of patient. We therefore propose the following adaptation to non-linear out-of-plane paths. Firstly, the back-projection is performed as expressed in equation 5 except that ray paths are back-projected along non-linear trajectories through the 3D volume and may pass through multiple axial slices. Secondly, the filtering operation, as described in equation 6 is performed slice by slice as if the protons had progressed linearly, parallel and in-plane.

Figure 7:
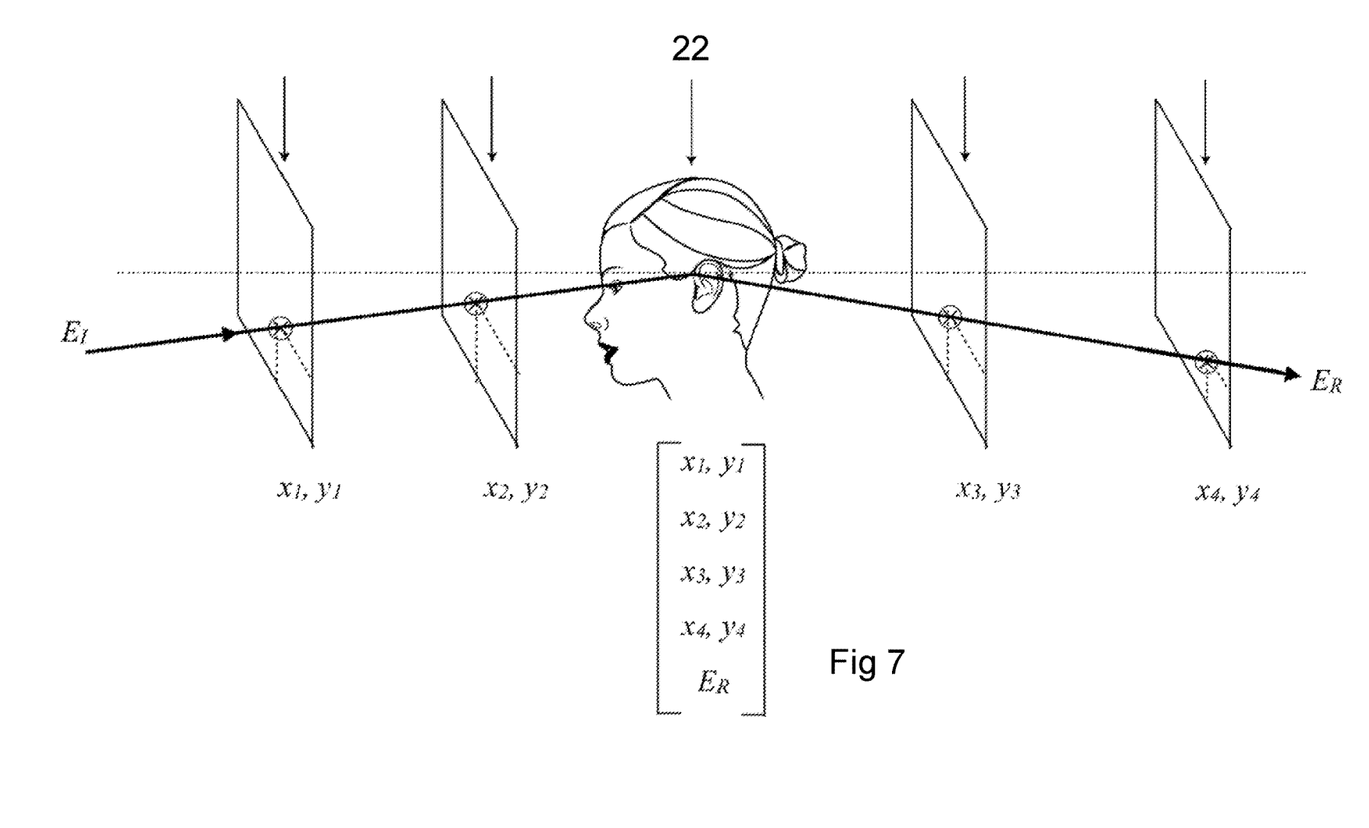
FIG. 7 shows a hypothetical path of a proton through position-sensitive detectors in an embodiment of the invention during imaging of a person.

The main elements of the proton CT system embodying the invention are shown in FIG. 7. In this example, there are two sets of position sensitive detectors 30, 32 in front of a patient 22 (the "object" that is being imaged), and there are two sets of position sensitive detectors 34, 36 after the patient 22. The input vector, for an individual proton with initial energy $E_I$, to the BPF algorithm consist of four sets of positional data obtained from the sets of detectors 30 ... 36 $\{(x_1, y_2), \ldots, (x_4, y_4)\}$ and the residual energy of the proton, $E_R$, as recorded by an energy-sensitive detector 18 in FIG. 1. The path of the proton shown in FIG. 7 is a diagrammatic example only.

Figure 8:
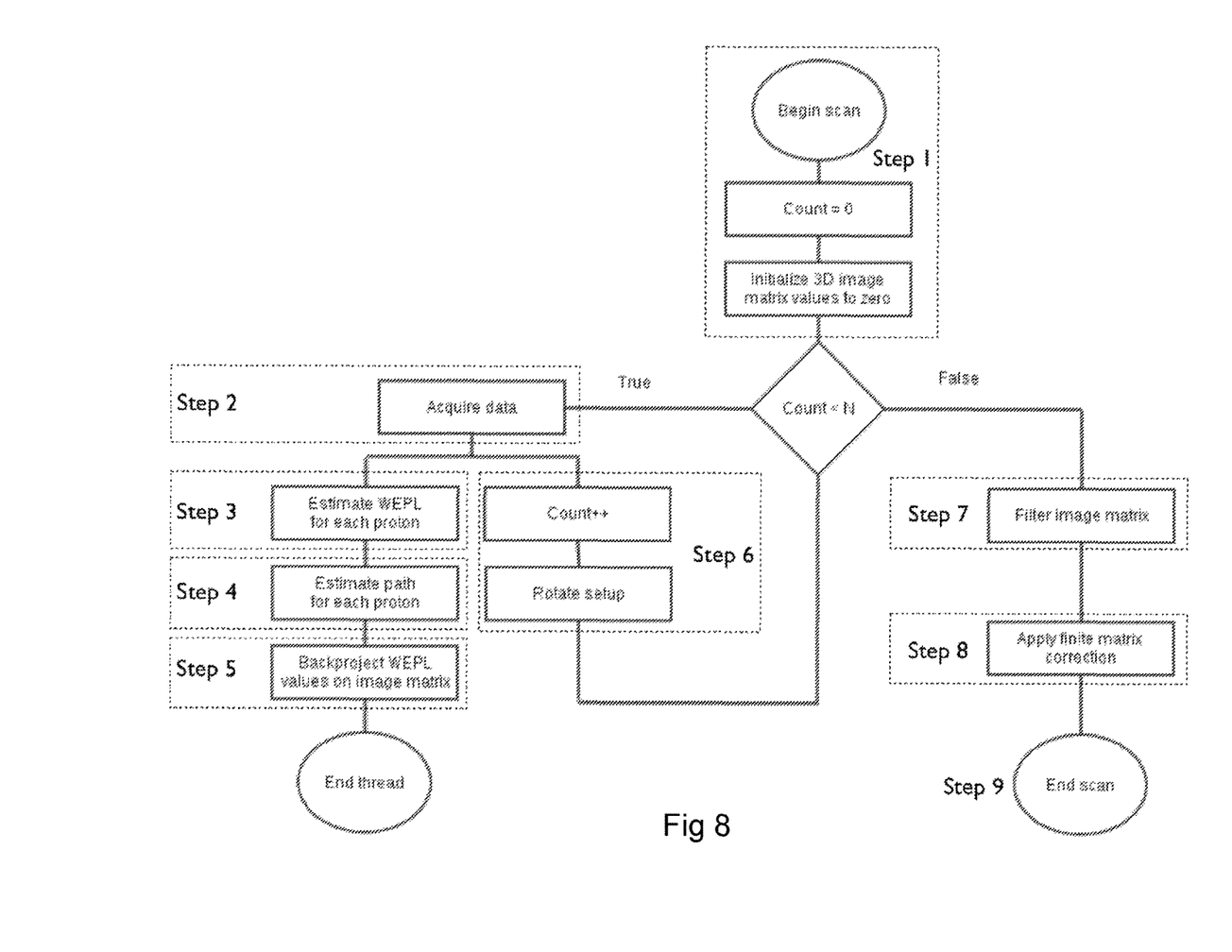
FIG. 8 is a flow diagram that describes the steps carried out in a process embodying the invention.

With reference to FIG. 8, the sequence of operations for the generation of a proton CT image in an embodiment of the invention will now be described.

In Step 1, the number of rotations, N, is set and the Count initialised to zero. The values of the CT image matrix are also set to zero.

In Step 2, data is acquired from the instrument (at the initial scan angle). This individual projection data consists of the recorded vector for each identified individual proton path and its residual energy, $E_R$, that is:

$$\begin{bmatrix} x_1, y_1 \\ x_2, y_2 \\ x_3, y_3 \\ x_4, y_4 \\ E_R \end{bmatrix}$$

Proton energies are converted in Step 3 into water-equivalent path lengths (WEPL), to preserve the uniform dimensionality of all parameters. There are several ways to achieve this conversion. In this example:

$$WEPL_R = R_{H_2O}(E_I) - R_{H_2O}(E_R)$$

where $R_{H_2O}(100)$ is the range in water of a 100 MeV proton, and $E_1$ is the initial energy of the proton.

As a first option, $$WEPL_R = -\int_{E_I}^{E_R} SP_{H_2O}(e)^{-1} de,$$

where $SP_{H_2O}$ is the stopping power for protons in water.

Or as a second option, $$WEPL_R = f(E_I, E_R),$$

where $f(E_I, R)$ returns the most probable value for WEPL, given the initial energy $E_I$ and estimate residual range, $E_R$, from the energy-sensitive detector. The function $f(E_I, R)$ can be calculated from Monte Carlo simulations or from calibration experiments.

It has been found that these three different approaches should provide answers that differ by less than 1%. The vector is now:

$$\begin{bmatrix} x_1, y_1 \\ x_2, y_2 \\ x_3, y_3 \\ x_4, y_4 \\ WEPL_R \end{bmatrix}.$$

Figure 9:
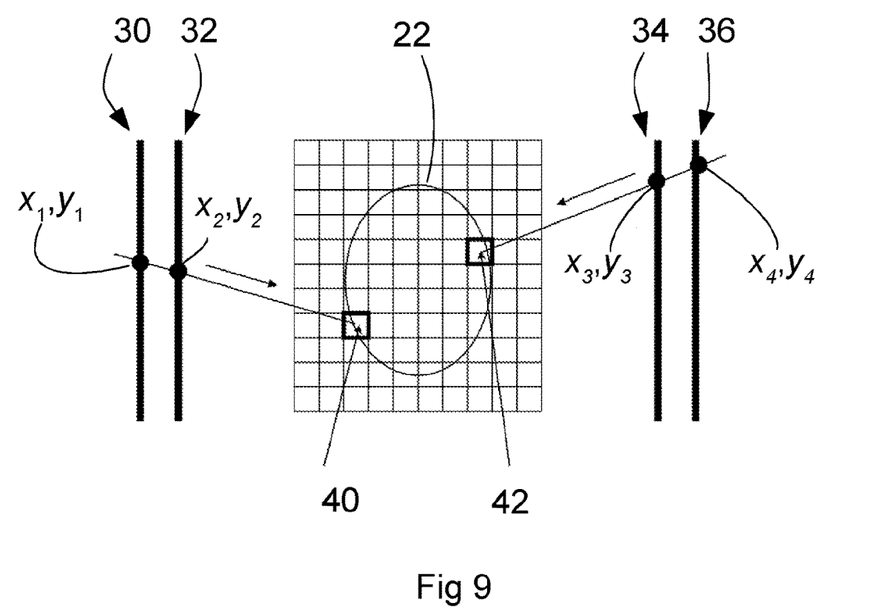
FIG. 9 illustrates the points of interaction between a proton, position-sensitive detectors, and a person being imaged in an embodiment of the invention.

Step 4 is to estimate the path of each proton through the patient 22. As illustrated in FIG. 9, this is done by projecting forward and backward from the respective (x, y) locations of the appropriate detectors 30 ... 36 to determine the entry and exit voxels 40, 42 for the reconstruction. Protons experience multiple Coulomb scattering (MCS), so superior final image quality can be achieved if this is taken into account instead of assuming a straight-line path. Several methods are available to estimate the most likely path, for example:

Most Likely/Probable trajectory: for each of the two lateral directions, estimate the most likely displacement and direction vector for each proton at each z location along the beam axis (R. W. Schulte, et al, *A maximum likelihood proton path formalism for application in proton computed tomography*, Med. Phys. 35, 4849, 2008).

Most Likely/Probable position: for each of the two lateral directions, estimate the most likely displacement for each proton at each z location along the beam axis (D. Wang, T. R. Mackie and W. A. Tomé, *On the use of a proton path probability map for proton computed tomography reconstruction*, Med. Phys. 37, 4138, 2010).

Approximate the path empirically using a smooth transition between the initial and final proton vectors e.g., cubic spline (D C Williams, *The most likely path of an energetic charged particle through a uniform medium*, Phys. Med. Biol. 49, 2899, 2004).

Figure 10:
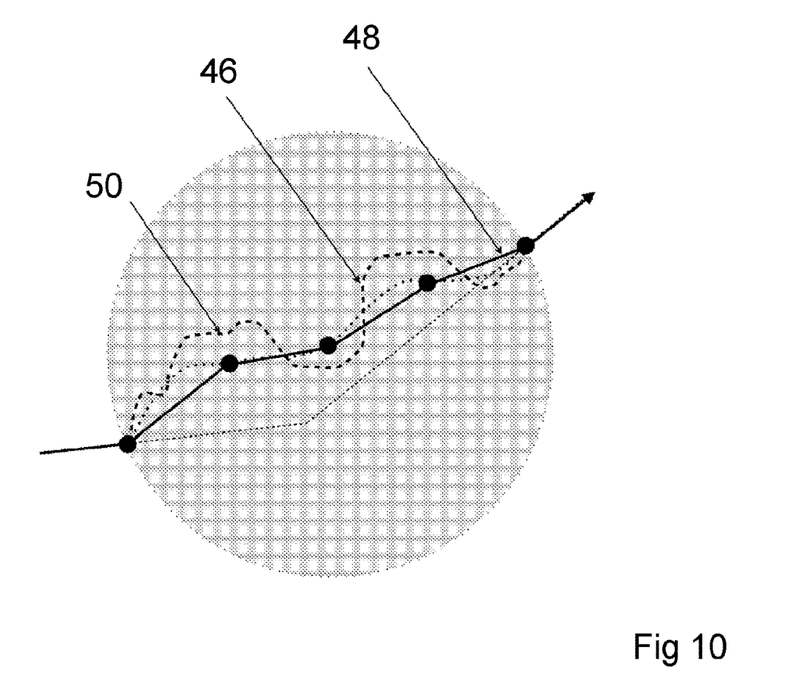
FIG. 10 illustrates a possible path of a proton and corresponding path models during imaging of a person in an embodiment of the invention.

Any of the above methods, or another, can be used to estimate the most likely path of an individual proton through reconstruction matrix. A smooth (non-linear) path 46 or a piecewise linear representation 48 of the actual path 50 can be used (illustrated in FIG. 10) in respect to any of the above methods.

Figure 11:
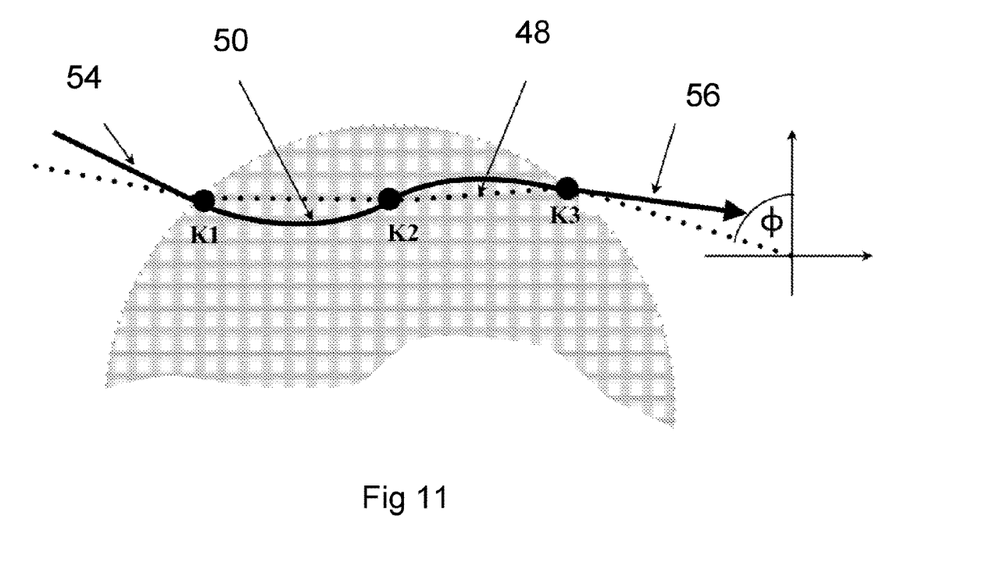
FIG. 11 illustrates a path of a proton through an object, and the model of the path using a spline.

For example, an n-knot spline may be employed to model the proton path 50, the inside the object. For each proton, n knot points K1, K2, K3 are equally spaced between phantom entry and exit points 54, 56. Inside the object, back-projection is assumed linear between any two knot points, as shown in FIG. 11. Outside the object, the protons are projected back from the surface with trajectories parallel to the beam axis (at an angle φ in the x-y plane). This prevents the back-projection rays "spreading-out" as they diverge from the object. Back-projecting away from the object into empty space along the actual entry and exit trajectories can result in a small quantitative error in the reconstructed stopping powers of up to 1%.

In Step 5, the associated $WEPL_R$ values are back-projected into the image matrix. The relevant formulation is Eqn. (5).

Steps 2 to 6 are repeated until Count=N.

In step 7, the filtering operation given by Eqn. (8) is performed on the completed back-propagation matrix, b(x, y).

In step 8, the Finite Matrix Correction factor, C, (Eqn. 10) is calculated and applied in accordance with Eqn. (11).

Finally, in step 9, the proton CT image can be displayed.

Although embodiments of the invention have been described with reference to the use of protons, applications of the invention are not limited to tomography using protons. Alternative embodiments might use any particles that lose energy quasi-continuously as it passes through matter such as helium or heavier ions. The finite matrix correction and kernel for BPF would also be applicable to x-ray CT, single-photon emission computerised tomography and positron emission tomography.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers or characteristics described in conjunction with a particular aspect, embodiment or example of the invention are to be understood to be applicable to any other aspect, embodiment or example described herein unless incompatible therewith.

The invention claimed is:

1. A method of reconstructing a 3-dimensional computerised tomography image, the method comprising:
   a. creating an image reconstruction matrix by:
      from a plurality of scan angles surrounding an object to be imaged:
         i. directing a plurality of particles to traverse the object; and
         ii. measuring a trajectory and energy of each particle before and after each particle has traversed the object;
         iii. for each particle, calculating an equivalent path length (EPL) within the object; and
         iv. calculating an entry position at which each particle entered the object and an exit position at which each particle exited the object; and
   b. adding the EPL to the entry and exit positions of each particle of the image reconstruction matrix or a subset of elements thereof;
   c. applying a spatially varying 2-dimensional filter function to the image reconstruction matrix to generate a filtered reconstruction matrix;
   d. applying a correction factor to the filtered reconstruction matrix to at least partially correct for a finite extent of the filtered reconstruction matrix, and
   e. reconstructing the 3-dimensional computerised tomography image from the filtered reconstruction matrix.

2. The method of claim 1, wherein the particles comprise protons, other hadrons or ions.

3. The method of claim 1, wherein the particles comprise protons.

4. The method of claim 1, wherein the EPL is the EPL in a reference material.

5. The method of claim 1, wherein the EPL is a water-equivalent path length.

6. The method of claim 1, wherein the trajectories of individual particles before traversal of the object are recorded by a multiplicity of position-sensitive detectors that are encountered by the particles before they encounter the object.

7. The method of claim 1, wherein the trajectories of individual particles after traversal of the object are recorded by a multiplicity of position-sensitive detectors that are encountered by the particles after they have encountered the object.

8. The method of claim 1, wherein each measured particle trajectory is traced back to create the image reconstruction matrix, and there is deposited at each location within this image reconstruction matrix corresponding values of an integral:

$$b(x, y) = \int_{-R}^{R} \int_0^{\pi} dt d\theta p(t, \theta) \delta(x\cos\theta + y\sin\theta - t) = \int_0^{\pi} d\theta p(t, \theta)\Big|_{x\cos\theta + y\sin\theta = t},$$

wherein $p(t,\theta)$ is a Radon transform related to a line at an angle $\theta$ from a y-axis and at a distance $|t|$ from the origin.

9. The method of claim 8, wherein creating the image reconstruction matrix is completed prior to any filtration being applied to its contents.

10. The method of claim 1, wherein the image reconstruction matrix is subject to a band-limited convolution kernel in which a sampling pitch of the matrix is imposed on the convolution kernel in a frequency domain.

11. The method of claim 10, wherein an additional smoothing filter is applied by sampling an appropriate function in the frequency domain and multiplying the convolution kernel.

12. The method of claim 11, wherein the additional smoothing filter is a Shepp-Logan or a Gaussian filter.

13. The method of claim 1, wherein a back-projected image matrix is given by:

$$b(i, j, k) = \frac{\pi}{L} \sum_{m=1}^{L} \frac{\sum_{n=1}^{K} \lambda_{n,m}(i, j, k) WEPL_{n,m}}{\sum_{n=1}^{K} \lambda_{n,m}(i, j, k)},$$

wherein $\lambda_{n,m}(i, j, k)$ is a path length of an $n^{th}$ proton in an $m^{th}$ projection through a voxel $(i, j, k)$, L is a number of projection angles, K is a number of recorded projections per angular position, and $WEPL_{n,m}$ is a water-equivalent path length for the $n^{th}$ proton in the $m^{th}$ projection.

14. The method of claim 13, wherein step c. further comprises convolving the back-projected image matrix with a 2-dimensional filter function.

15. The method of claim 14, wherein the 2-dimensional filter function has the form:

$$k(r) = \frac{1}{4\pi^2 r^3} \left[ \left(\frac{\pi r}{\tau}\right)^2 J_1\left(\frac{\pi r}{\tau}\right) - \Phi\left(\frac{\pi r}{\tau}\right) \right],$$

wherein $\tau$ is the matrix pitch, where $$\Phi(x) = \frac{\pi x}{2}[J_1(x)H_{0(x)} - J_0(x)H_{1(x)}]$$

and $J_n$ and $H_n$ are $n^{th}$ order Bessel and Struve functions, respectively.

16. The method of claim 1, wherein the correction factor is $$\Delta = \left( \tau^2 \sum_{pixels \in \Omega_f} f(i, j) \right) \left( \tau^2 \sum_{pixels \notin \Omega_b} \frac{k(N/2 - i, N/2 - j)}{\tau \sqrt{i^2 + j^2}} \right)$$

wherein $\tau$ is the matrix pitch and i, j, and k are coordinates of a voxel $(i, j, k)$.

17. The method of claim 1, wherein a further correction factor is applied to further reduce residual errors in the filtered reconstruction matrix to stop powers that arise from trajectories of particles exiting the object that are not parallel to a collimation of an axis of an incident particle beam.

18. The method of claim 1, further comprising:

displaying the proton computerised tomography image.

19. A computerized tomography apparatus, comprising:

a source of particles;

a first multiplicity of position-sensitive detectors configured to detect a position and energy of particles prior to the particles traversing an object;

a second multiplicity of position-sensitive detectors configured to detect the position of the particles prior to the particles traversing the object; and a computer system configured to reconstruct an image of the object by analysis of output of the first and second multiplicity of position-sensitive detectors using the method of claim 1.

20. The apparatus of claim 19, wherein a back-projected image matrix is given by:

$$b(i, j, k) = \frac{\pi}{L} \sum_{m=1}^{L} \frac{\sum_{n=1}^{K} \lambda_{n,m}(i, j, k) WEPL_{n,m}}{\sum_{n=1}^{K} \lambda_{n,m}(i, j, k)}$$

wherein $\lambda_{n,m}(i, j, k)$ is a path length of an $n^{th}$ proton in an $m^{th}$ projection through a voxel $(i, j, k)$, L is a number of projection angles, K is a number of recorded projections per angular position, and $WEPL_{n,m}$ is a water-equivalent path length for the $n^{th}$ proton in the $m^{th}$ projection.

* * * * *